(12) United States Patent  (10) Patent No.: US 8,109,134 B2
Casagrande  (45) Date of Patent: Feb. 7, 2012

(54) NONDESTRUCTIVE METHODS FOR TESTING THE DEGREE OF HARDENING OR DRYING OF INKS AND COATINGS

(75) Inventor: Magdalena-Elena Casagrande, Munich (DE)

(73) Assignee: manroland AG, Offenbach (DE)

( * ) Notice: Subject to any disclaimer, the term of this patent is extended or adjusted under 35 U.S.C. 154(b) by 871 days.

(21) Appl. No.: 12/058,162

(22) Filed: Mar. 28, 2008

(65) Prior Publication Data

US 2008/0240762 A1 Oct. 2, 2008

(30) Foreign Application Priority Data

Mar. 28, 2007 (DE) .......................... 10 2007 015 366
Jun. 30, 2007 (DE) .......................... 10 2007 030 566

(51) Int. Cl.
*B23Q 17/20* (2006.01)
(52) U.S. Cl. ........................................................ 73/78
(58) Field of Classification Search .................. None
See application file for complete search history.

(56) References Cited

U.S. PATENT DOCUMENTS

| 4,312,228 A | | 1/1982 | Wohltjen | |
|---|---|---|---|---|
| 4,536,184 A | * | 8/1985 | Ryan | ................................ 8/508 |
| 6,145,948 A | * | 11/2000 | Kishida | ........................... 347/13 |
| 6,151,796 A | * | 11/2000 | Karamatsu et al. | ................ 34/92 |
| 2004/0107869 A1 | * | 6/2004 | Velamakanni et al. | ..... 106/31.92 |
| 2008/0044543 A1 | * | 2/2008 | McClements et al. | ......... 426/573 |

FOREIGN PATENT DOCUMENTS

| DE | 24 58 935 A1 | | 6/1975 |
|---|---|---|---|
| DE | 30 45 581 A1 | | 8/1981 |
| DE | 43 18 445 A1 | | 12/1994 |
| DE | 197 37 785 A1 | | 3/1999 |
| DE | 103 18 104 A1 | | 11/2004 |
| DE | 10 2005 009 262 A1 | | 8/2006 |
| EP | 1 142 711 B1 | | 10/2001 |
| GB | 2219858 A | | 12/1989 |
| JP | 64-27672 | * | 1/1989 |
| JP | 7-169337 | * | 7/1995 |
| JP | 11-218481 | * | 8/1999 |

* cited by examiner

*Primary Examiner* — Robert Raevis
(74) *Attorney, Agent, or Firm* — Leydig, Voit & Mayer, Ltd.

(57) ABSTRACT

In a method for determining the degree of hardening or drying of one or more printed ink and/or coating film(s) on a substrate, for instance, paper, cardboard, plastic film or composite materials, a faster and more efficient measuring method can be found that furthermore supplies secure and easily interpreted results. The method is to be used in the mass production printing processes comprising intaglio printing, flexographic printing, screen printing or offset printing. The degree of hardening or drying is determined indirectly by way of the change in the mechanical and/or viscoelastic properties of the ink and/or coating films on the substrate that result from the hardening or drying process. The detection of acoustic waves by means of a piezoelectric sensor is used as the measuring method.

25 Claims, 6 Drawing Sheets

NONDESTRUCTIVE METHODS FOR TESTING THE DEGREE OF HARDENING OR DRYING OF INKS AND COATINGS

RELATED APPLICATIONS

This application claims priority to German Application No. 102007030566.6 filed Jun. 30, 2007 and German Application No. 102007015366.1 filed Mar. 28, 2007, which herein are incorporated by reference in their entireties for all that they teach without exclusion of any portion thereof.

FIELD OF THE INVENTION

The invention relates generally to a method for testing by means of ultrasound the degree of hardening of ink or coating films used in one of the mass production printing methods comprising offset, flexographic or intaglio printing.

BACKGROUND OF THE INVENTION

The hardening of ink and coating films can take place by evaporation of solvents, by absorption of solvents in the substrate, by oxidation, by polymerization in UV or electron beam dryers, or by a combination of the above-mentioned drying mechanisms.

Many factors argue for monitoring the hardening of ink and coating films. A sufficient drying or hardening of the printed inks/coatings is a prerequisite for high-quality printing. Inside the conveyance path of sheets through a machine, contact of the freshly printed or coated sheet surface can lead to damage, which results in print soilage. The sheets in the delivery unit of a sheet-fed printing machine, or the rolled up webs of a web-fed printing machine must be sufficiently dry with respect to the printed inks/coatings, since otherwise they would become smudged and stuck together during stacking or winding. The latter in particular would hinder further processing of the printed products or render it impossible.

Strict requirements must be placed on the adjustment of differently constructed dryer units. When the printing machine is being set up, the user must make adjustments to the dryer units in order to be able to produce the necessary quality within as short a time as possible and with as small a number of wasted sheets (feeding waste) as possible. An excessively high setting of the dryer power not only causes high power consumption of the printing machine and likewise a large waste of heat power, which would raise the temperature of the printing room or have to be adjusted to the predetermined value by the air-conditioning unit of the printing room, but also negatively affects the printing process itself. It is known that the tack and viscosity of ink/coating vary, so that under certain circumstances a high heating of the machine as well as the heating of the ink and the metering device could require re-regulation, causing waste. Excessively low settings for the dryer action or dryer power must likewise be avoided, since otherwise the above-described danger of smudging of freshly printed sheets during sheet transport or in the delivery device exists.

By controlling the dryer, it is possible not only to reduce print spoilage, but also to save considerable energy. Since the dryer devices are only operated at the power that is necessary according to the current situation, the power consumption of the devices is reduced to the respective required value. Reduced heating of machine elements or the entire machine results, because the dryer devices also reduce waste heat. The service life of the machine or of machine components is thereby increased. Finally, a reduced dryer power also avoids raising the printing room temperature. For an air-conditioned room this likewise provides energy savings since less waste heat is produced by the dryer.

Special issues arise for the printing of radiation-hardening inks and coatings in printing machines, which require monitoring of the hardening. Printing with radiation-hardening offset ink has become widely disseminated and is well known. The advantages of printing with radiation-hardening inks lie in the rapid spontaneous polymerization after irradiation with a UV radiation source, the lack of solvents in the ink, and the good printability of non-absorptive substrates.

Conventional inks, on the other hand, are either oil-based or contain solvents. Oil-based inks dry by oxidation of the oil-based binders, or they dry by evaporation of the easily volatilized oils in the ink (heat set method). In contrast, radiation-hardening inks and coatings are hardened by a photochemical process, also referred to as polymerization. The liquid or unpolymerized ink film is transformed into a solid state by polymerization under the influence of UV light.

Malfunctions are known, however, in which unpolymerized ink components are transferred to the back of the substrate above them by blotting in the delivery stack of a sheet-fed printing machine or by blotting in a reel after printing. Ink components can also migrate through the substrate. For packaging, migration of ink components or blotting of ink can lead to a sensory effect on the packaged material. If specific migration limits are exceeded in food packaging, harm to the health of consumers cannot be ruled out. If the specific migration limits are exceeded, packages must be withdrawn from the market, which, in addition to the financial consequences, results in lost reputation of the brand's manufacturer. Maintenance of harmlessness to health is paramount.

According to §30 LMBG [Food Safety Act], it is prohibited to manufacturer consumer articles in such a manner that, when used as directed, they are liable to be harmful to health due to their material composition, in particular, due to toxicologically active substances or contamination. Moreover, according to German and European law, and in the USA as well, the "no migration principle" applies, i.e., transfer of substances to the packaged foodstuffs must be avoided. Therefore, it is particularly important to ensure the polymerization of the radiation-hardening ink on the substrate in all cases.

Incompletely hardened radiation-hardening inks and coatings also have effects on the safety of the operating personnel. For example, if such ink or coating films on the substrate are not completely hardened and a machine operator takes samples to check the print quality, migration-capable components of the ink may be absorbed through the skin. In addition to health risks, irritation and allergic skin reactions can occur. The printing plant also incurs additional disposal costs from incompletely hardened coatings and inks, since printed sheets with unpolymerized ink or coating components must generally be treated as hazardous waste. This requires extra logistical effort and generates excess costs for disposal.

Many factors therefore suggest that the hardening or drying of ink and coating films on the substrate should be measured, measurement parameters formed, and they should be used to control the dryer directly or via user input. Additionally, a quality protocol can be formed from these measured values, which will give the end-user verification that the ink or coating has been sufficiently hardened. This is often demanded specifically in the field of radiation-hardening inks and coatings.

The desire to evaluate the hardening or drying of ink and coating films has already been widely discussed. In EP 1 142 711 B1 it was proposed among other things that a controller be provided for the dryer device, to which at least one signal of a parameter characterizing the printing process is supplied, and that, consequently, the controller generate signals for varying the operating mode of the dryer device in a predetermined manner. It is also proposed to undertake the controlling of the dryer unit on the basis of values measured on the substrate. The coating or ink film thickness and/or the gloss of the applied coating are mentioned as measurement parameters.

DE 19 737 785 A1 proposes to determine the degree of dryness of a coating film by measuring the intensity of a microwave signal that interacts with the coated substrate. The state parameter formed from the measurement signal can then be utilized as a control parameter for controlling the dryer. However, the method is suitable only for use of coating media that absorb microwave energy to a large extent, such as dispersion varnish, which has essentially only water as a solvent. Testing the polymerization of hardened ink and coating films was not mentioned in the patent.

DE 24 58 935 A1 discloses a method for measuring and controlling the speed of printing and coating machines, in which the wavelengths corresponding to the solvents that are used are continuously analyzed on the paper webs, with the average values measured after drying being compared to the preset maximum values. The measurement unit contains an analyzer head with continuous emission of radiation and a receiver for receiving the radiation that the product to be analyzed reflects or that passes through the latter. The disadvantage of this method is that the solvent composition must be known in advance. This is relatively simple for printing processes that operate with simple solvent compositions, but the complexity increases for modern ink with a number of solvents. The supplier generally discloses the composition of the ink only in approximate amounts of the constituents. This method also fails for printing processes that do not emit any solvent. These include, among others, radiation-hardening printing processes, as well as oxidative and ink-absorption processes. This measurement method is not universally applicable. Moreover, using it for fast-running printing machines is not known, since the analysis is time-intensive and complex.

Optical spectroscopy is used in the laboratory for assessing polymerization. Due to its complexity and the required preparation of specimens, this method is not well-suited for use in the rough machine environment of a printing plant. Ultrasound measurements are known as a measuring method in the printing industry. Test methods with ultrasound have the advantage that they are noninvasive and nondestructive techniques for determining the properties of a material.

One known approach for checking the strength of paper webs is the measurement of the propagation velocity and intensity of acoustic waves in these materials. Such a method and a device for nondestructive examination of paper in a continuous, rapidly moving web during manufacturing are described in DE 3 045 581 A1. This method exploits the fact that many strength parameters of paper are related to a modulus of elasticity. The latter can be correlated with the velocity of acoustic waves propagating through the paper web.

A transmitting acoustic source or transducer transmits a mechanical signal to the paper, and a receiver receives the ultrasound signal from the paper. With knowledge of the time that ultrasonic signals require for propagation through the paper and of the distance that these acoustic waves travel, the velocity of the acoustic waves can be calculated. The transducers are arranged according to this invention on wheels that are in physical contact with the paper web. Because of this contact and the strict requirements for synchronization of the wheels, the invention is not very practical. Such a measurement on printed paper webs appears to be very difficult due to the contact.

A measurement in which there is a non-contacting coupling of acoustic waves would therefore be desirable. As a non-contacting measurement of the flexibility of banknotes, DE 103 18 104 A1 proposes irradiating them with acoustic waves, detecting the acoustic waves coming from the sheet material, measuring the transmitted and reflected acoustic waves, and deriving values for the flexibility of the sheet material therefrom that are independent of the degree of soiling of the banknote. The disadvantage of the solution that was found is, among other things, that the acoustic receivers are arranged on both sides of the paper. Moreover, only transmitted or reflected acoustic waves are evaluated; the propagation of the acoustic waves on the surface is not taken into account.

Assessment with SAW (surface acoustic waves) is also known in science as a method for nondestructive testing processes.

OBJECTS AND SUMMARY OF THE INVENTION

The objective of the invention is to determine the hardening or drying of coating and ink films on papers, films or cardboard substrates.

This problem is solved by the characteristics of claim 1. Practical refinements of the invention follow from the subordinate claims.

The waves induced in the surface propagate as surface waves at a velocity of several kilometers per second on the surface of the solid body. Inferences regarding a wide variety of parameters of influence on the surface can be drawn, both qualitatively and quantitatively, from the transit time and attenuation of the surface wave signals.

The mechanical deflection and all other parameters accompanying the surface wave decay exponentially within roughly one wavelength into the bulk of the material. The concentration of acoustic energy at the surface (and the characteristic physical parameters that can thereby be observed) therefore make surface waves extremely interesting for sensor systems.

The method is also distinguished by the following characteristic features:

External influences can be recognized early, since changes are detected directly on the boundary surfaces with the exterior. The influences measured in practical applications are usually of an electronic or mechanical nature.

The restriction of the parameters accompanying the wave to the surface makes the sensor extremely sensitive, even to relatively small influences.

The wavelength of the surface wave generated in this way is several orders of magnitude above the atomic distances in the ink or coating film.

The invention will be described below on the basis of several graphical and schematic representations.

Other objects and advantages of the invention will become apparent upon reading the following detailed description and upon reference to the drawings, in which:

While the invention is susceptible of various modifications and alternative constructions, a certain illustrative embodiment thereof has been shown in the drawings and will be described below in detail. It should be understood, however, that there is no intention to limit the invention to the specific form disclosed, but on the contrary, the intention is to cover all modifications, alternative constructions, and equivalents falling within the spirit and scope of the invention.

DESCRIPTION OF THE PREFERRED EMBODIMENTS

Figure 4:
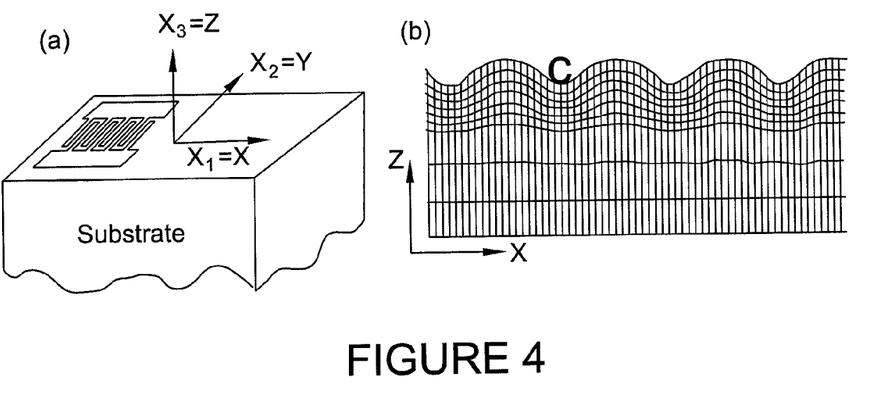
FIG. 4 shows a graph of the propagation of the surface wave in the X-direction.
Figure 5:
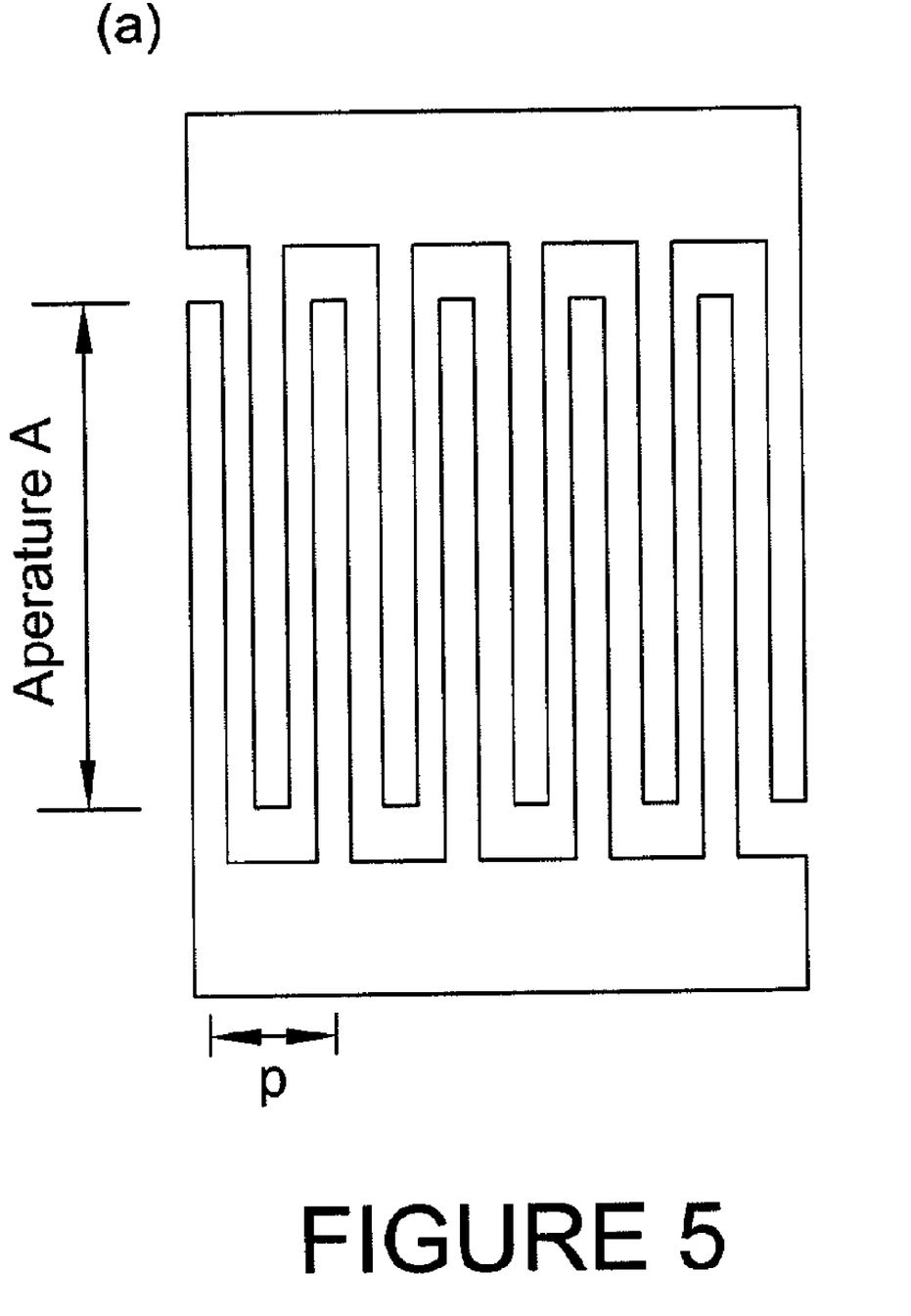
FIG. 5 shows a comb-like electrode structure with the corresponding aperture.
Figure 6:
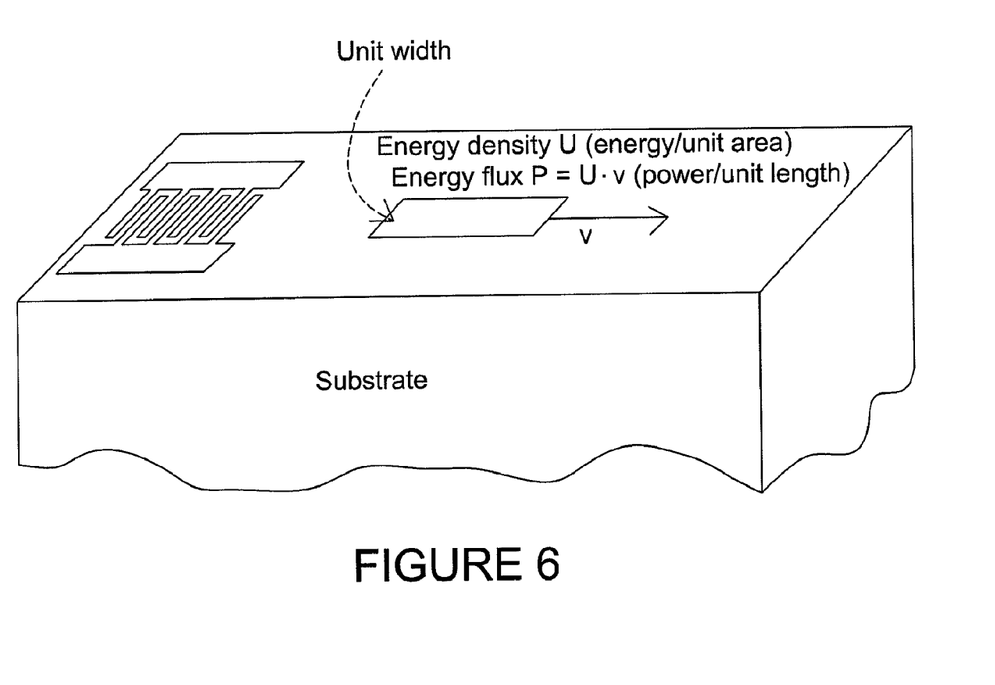
FIG. 6 shows a graph of the energy flux and the energy flux direction of a surface wave.

The surface wave is generated and detected with a piezoelectric material, the control voltage and the obtained signal being introduced and read out, respectively, via a comb-like electrode structure applied to the piezoelectric material. These are also referred to as interdigital acoustic transducers (IDT). The individual teeth of the comb-like structure reach between one another, as shown in FIGS. 4-6, and particularly FIG. 5. One comb structure serves here as an actuator, via which the acoustic waves are induced in the material, and the opposing second comb structure acts as a sensor. A high-frequency electromagnetic alternating current is applied to the comb structure serving as the actuator. The inverse piezoelectric effect ensures that the substrate is alternately elongated and compressed. These density modulations propagate at the speed of sound, and receive an additional amplifying modulation at the next pair of fingers if the resonant condition $f=\lambda/v$ is satisfied between applied frequency f, speed of sound v and wavelength $\lambda$. The spacing between the individual fingers, also referred to as aperture A, determines the wavelength and thus has an influence on the sensitivity. The frequency at which an acoustic wave can be excited is determined by the thus-described arrangement, together with the speed of sound.

The surface wave is likewise detected with the piezoelectric effect using such an electrode structure, after the surface wave has propagated from the generating to the detecting acoustic transducer. These transducers thus first translate an electromagnetic signal into an electromechanically coupled motion, which is translated back into a high-frequency electromagnetic signal after the transit time has elapsed. The manner in which the back-translated signal is related to the input signal is decisively determined by the acoustic transducer structure.

A surface wave is generated that propagates along a narrow acoustic track. The position of the acoustic path can be defined or adjusted along the aperture A by the frequency. The area between the acoustic transducers can be scanned by passing through a frequency range between the minimum and the maximum resonant frequency, corresponding approximately to sensing between the largest and smallest periodicity, p0 and p1 respectively. If a change takes place between the transmitting and the receiving acoustic transducer, the effect is visible in the difference of the transmission signal before and after the change. If one combines this measurement with the sensing of the frequency, the spatial position of the change can be determined in one direction along the aperture A.

The velocity of the surface wave on a piezoelectric substrate depends on the various material parameters. An analytical expression for the coupling coefficient as a function of the material parameters can be found, but one can assume that, analogously to the coupling coefficient for the bulk acoustic wave mode, it depends on the mechanical, piezoelectric and dielectric constants.

A sensor is intended to acquire the changes to be detected in the best manner possible in order to allow inferences to be drawn regarding the material parameters that participate in determining the propagation velocity of the surface wave. The character of the wave propagation (wave attenuation, wave propagation velocity) can be further influenced by additional coatings.

The interactions between the surface wave and the material film to be measured are either of a mechanical or an electrical nature. In the case of a mechanical interaction, the variation of the elastic constant and/or the mass density are observed. The electrical interaction can be observed by the piezoelectric fields that accompany the mechanical deflections through the surface (see FIG. 4).

These measuring methods are also suitable for determining the material properties of extremely thin films on a carrier substrate. In printing, thin ink and coating films in a thickness range of 0.75-6 μm are applied to paper and plastic as the carrier material. Hitherto the determination of material properties by means of surface waves has been applied only to markedly thicker layers.

During hardening (polymerization) or drying of the ink or coating film, the mass state and the associated viscoelastic properties of the ink or coating film undergo a change.

The greatest part of the surface wave's energy lies in the density modulation of the material to be measured. A direct external effect on the density modulation therefore likewise has a strong effect on the surface wave and can thus be made measurable.

If one considers the ink or coating film in a model construction as a material consisting of individual points of mass connected to one another by springs, then the density modulation results from the collectively oscillating points of mass. Changes in the mass of the points or a change of the spring constant has an effect on the density modulation and thus on the acoustic wave. The relevant density measurement is not the volume mass density, but the surface mass density.

The latter can be changed by additional mass, because of a stronger cross-linking due to polymerization, for instance. The surface wave has an initial energy, which it loses along the propagation path. This energy loss is used to determine isotherms and can be observed as a first parameter. The dependence of the elastic constants of the film on the surface are specified, in addition to the pure increase of mass; i.e., ultimately viscoelastic effects are being dealt with.

The surface wave transports energy, whose associated energy flux P (power/unit length) corresponds to the intensity of the surface wave. The energy flux is dependent on the energy density U (energy/unit area) and velocity of the flux, which corresponds to the velocity of the surface wave (see FIG. 6). The intensity can be described by the following equation:

$$P = U \cdot v$$

and remains constant over the entire transit path, neglecting energy dissipation. If the energy density changes on the transit path of the wave, then the wave velocity must change.

The hardening of the ink or coating film results in a change in the mass of the ink or coating film. For a thin, non-volatilizing ink or coating film, the course of the hardening or drying process can be determined by observing the mass behavior due to the change in the mechanical and viscoelastic properties.

Surface acoustic waves are generated and detected with so-called interdigital acoustic transducers. Electric fields accompany mechanical deflections of the wave, whereby the surface waves react accordingly to electronic and mechanical influences. Moreover, the position of a narrow sound beam at the applied frequency can be adjusted by using fan-shaped transducer structures. A local effect on the surface can thus be sensed by the frequency, with position resolution in one dimension. We have investigated thin ink films in a film thickness range of 1-2 μm on the substrate with respect to the changes in the mass coating.

The film is located in the intersection area of two delay lines on the piezoelectric substrate. First, the nonlinear interaction between the surface waves propagating orthogonally to one another is examined with conventional acoustic transducers. The coupling exists if a surface wave noticeably modulates the charge carrier system for the mutually orthogonal surface wave in the intersection area. The charge carrier density can be determined from the magnitude of the coupling. With fan-shaped acoustic transducers the intersection area can be restricted to the width of the narrow acoustic paths. Each of these small intersection areas corresponds to a type of image element that can be driven or read out with the associated value pair of frequencies. The entire charge carrier density can be imaged by sensing the frequencies. Measurement results will be described in detail below.

Figure 1:
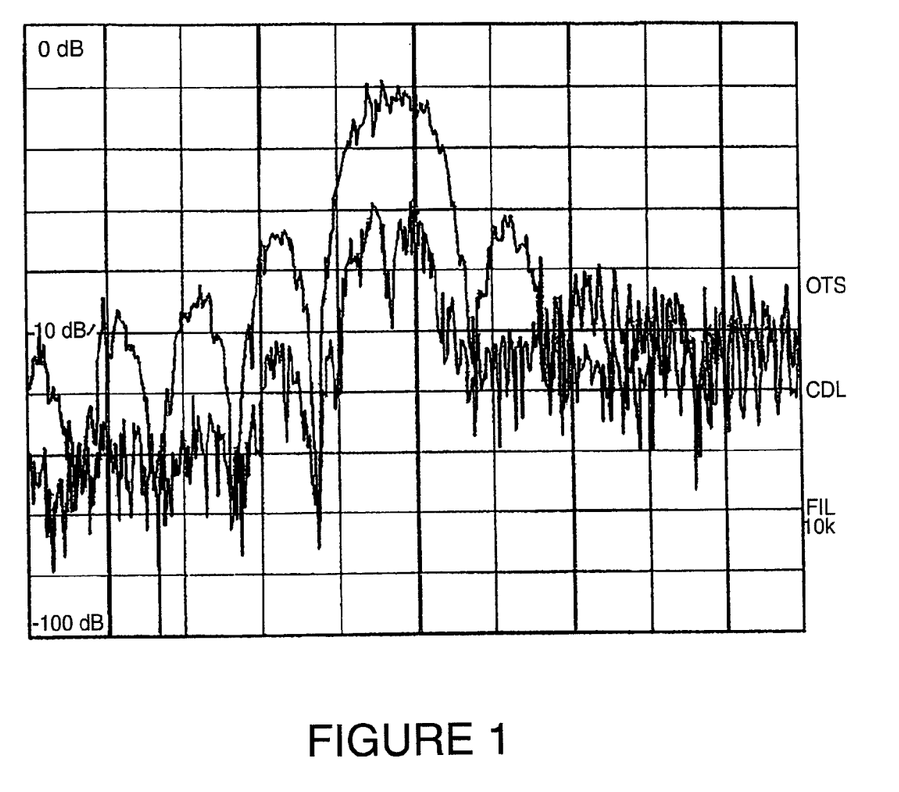
FIG. 1 shows a graph of the frequency spectrum (beginning of the irradiation with UV light for polymerization of the ink film; see center of the diagram)

The spectrum shown in a graph in FIG. 1 shows the wave frequency before and after irradiation, measured on a cyan and a magenta ink film of UV-hardening ink in an approximate ink film thickness of 1.5 μm. The UV measurement for this purpose takes place in situ, and the UV irradiation is turned on roughly in the center of the spectrum. It is evident here that the change of the spectrum due to UV-hardening and the associated hardening is very clearly recognizable, even to the untrained observer.

The measurement frequency can be determined by several reference measurements. It is found in this case that the measurement method functions only in a very narrow frequency range, but that clear signal changes are recognizable there. Polypropylene (PP) was used as a printing substrate, and a UV ink along with it.

Figure 2:
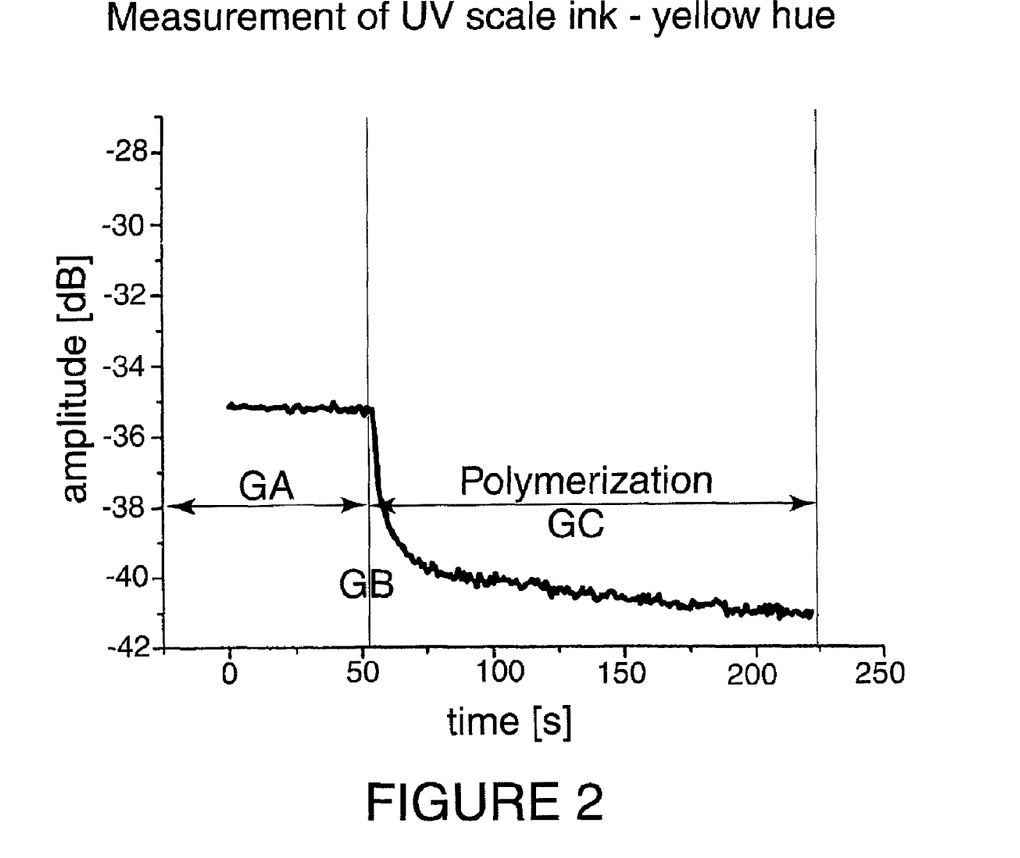
FIG. 2 shows a graph of the measured change of amplitude versus time (yellow hue)
Figure 3:
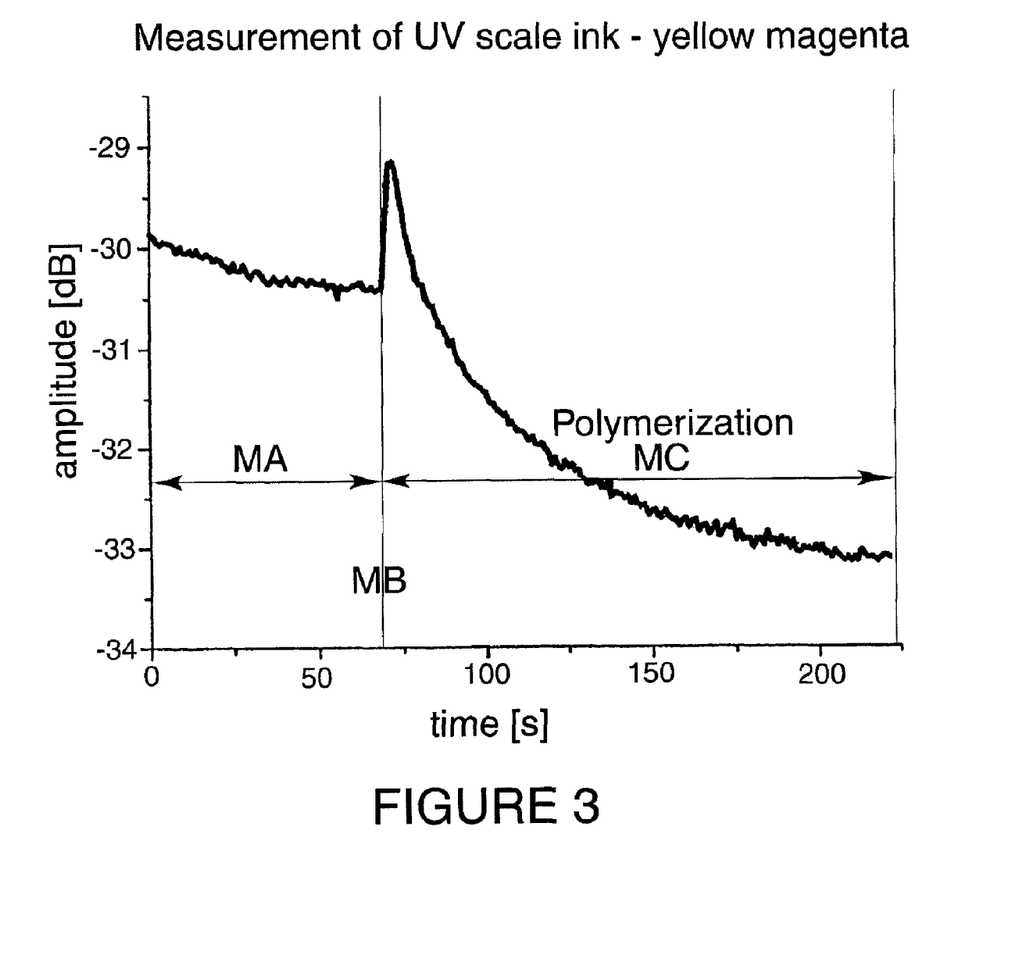
FIG. 3 shows a graph of the measurement of change in amplitude versus time (magenta hue)

The graphs in FIGS. 2 and 3 show the change in the amplitude of the surface wave over time. The graph in FIG. 2 shows the change for the yellow hue. Area GA describes the period of time before irradiation with UV light, GB the starting time of the irradiation, and GC shows the area of the progressing polymerization process under irradiation. The measurements were recorded in real time and show a very clear signal ratio before and after irradiation, from the values of which characteristic values for the degree and progression of the polymerization of the film can be derived. The graph in FIG. 3 shows the same curve for the magenta hue. The time period MA describes the time before the irradiation with UV light, point MB describes the starting time of the irradiation with UB light, and MC the area of progressive polymerization under UV irradiation.

This measurement was also carried out in situ in real time. It is clearly recognizable from the shape of the amplitude curve after the beginning of irradiation that the yellow hue hardens markedly faster than the magenta hue. This is also recognizable with other measurement methods such as real-time FTIR, but those measurement methods are relatively expensive and cannot be used in practice. The invented measurement method, on the other hand, is clearly more economical, easier to handle and can be used in production practice without a great amount of training.

The above-described measurements show the great advantage of this measurement method over others, such as optical measuring methods, since the method discovered according to the invention functions independently of the composition of the specimen. The method has never before been described for measuring thin printed ink and coating films in the typical thicknesses of 1-5 μm. Moreover, previous measurements started from solid materials or carrier bodies, so that the measurements achieved here offer significant scientific and technical progress in determining the degree of polymerization and the rate of polymerization. Characteristic values or control parameters for printing machines and/or drying and hardening units can be derived from these results in order to make energy-efficient and environmentally appropriate production possible. By classifying the hardening of an ink or coating film, the operator can also demonstrate a safe and quality-oriented production to the end user, a point that is becoming continually more important, given the controversies concerning product safety and the environment.

The invention claimed is:

1. A method for determining a degree of hardening or drying of one or more printed ink and/or coating films on a substrate selected from the group consisting of paper, cardboard, plastic film and composite materials, wherein a mass production printing processes selected from the group consisting of intaglio printing, flexographic printing, screen printing or offset printing is used, the method comprising:
   measuring a change in the mechanical and/or viscoelastic properties of the ink and/or coating films on the substrate resulting from the hardening or drying process wherein measuring the change in the mechanical and/or viscoelastic properties of the ink and/or coating films comprises generating a surface wave in the ink and/or coating film and measuring the energy density on the transit path of the surface wave; and
   determining the degree of hardening or drying indirectly based on the measured change in the mechanical and/or viscoelastic properties of the ink and/or coating films.

2. The method according to claim 1, wherein the surface wave is generated in a piezoelectric material on which an electrode structure with interdigitated comb-like substructures is arranged by the application of signals having a wavelength.

3. The method according to claim 2, wherein the electrode structure has two substructures whose individual teeth interpenetrate one another like fingers.

4. The method according to claim 3, wherein the electrode structure is connected to a controller by means of which a high-frequency electromagnetic signal can be applied to at least one substructure of the comb-like electrode structure in such a manner that an inverse piezoelectric effect leads to the substrate being alternately elongated and compressed.

5. The method according to claim 4, wherein the measuring characteristics of the comb-like electrode structure are determined by means of the spacing between the individual elements as an aperture.

6. The method according to claim 5, wherein the spacing between the individual elements of the comb-like electrode structure determines the wavelength of the signal.

7. The method according to claim 2, wherein the surface wave transports energy, and an energy flux associated with it is correlated with the intensity of the surface wave.

8. The method according to claim 7, further comprising accounting for losses of energy density on the transit path of the surface wave that lead to variations of the wave velocity.

9. The method according to claim 8, wherein the measurement is done on the basis that the energy losses take place as a result of the increase of the surface mass density of the coating.

10. The method according to claim 9, wherein the measurement is done on the basis that the change in viscosity of the ink or coating film is a consequence of the hardening of the film by radiation or drying.

11. The method according to claim 7, wherein the measurement is done on the basis that additional mass coating implies an increase of the viscosity of the measured film.

12. The method according to claim 2, wherein a high-frequency electromagnetic signal is applied to one substructure, whereby an inverse piezoelectric effect can be generated, by means of which the substrate is alternately elongated and compressed.

13. The method according to claim 2, wherein the wavelength of the signals is determined by means of the spacing between the interdigitated comb-like substructure.

14. The method according to claim 2, wherein a sound frequency at which the surface wave can be excited is determined in conjunction with the speed of sound.

15. The method according to claim 2, wherein the electrode structure functioning as an actuator translates an electromagnetic signal into an electromechanically coupled motion that, after passing through the material, is translated back into a high-frequency signal by the electrode structure functioning as a sensor, wherein the type of back-transformation of the signal correlates with the input signal that is determined by the electrode structure.

16. The method according to claim 1, wherein a surface wave that propagates on a narrow acoustic path is generated.

17. The method according to claim 1, wherein the measurement is done such that the position of an acoustic path along an aperture of the interdigitated comb-like substructures can be adjusted with frequency.

18. The method according to claim 1, wherein echoes of the surface wave in the transversal and/or longitudinal direction are detected.

19. The method according to claim 18, wherein changes to the acoustic wave are detected from the effect of the modification of one of the mass and spring constant of individual mass points on the density modulation.

20. The method according to claim 19, wherein one of a quantitative and qualitative value dependent on the elastic constants of the film on the surface is determined in the measurement from the variation of the mass.

21. The method according to claim 18, wherein a surface density provides a relevant mass density for measuring the surface wave, and the surface wave is variable by increasing a mass on the surface.

22. The method according to claim 1, wherein the surface wave has associated therewith an energy flux and an energy density, and wherein a surface wave velocity is acquired from a dependence of the energy flux on the energy density and a velocity of the energy flux, wherein the velocity of the energy flux corresponds to a velocity of the surface wave.

23. The method according to claim 1, wherein in a thin, non-volatilizing and nearly isotropic ink film, the progress of the hardening or drying process of the ink and/or coating film is observed on the basis of the change of the mechanical viscoelastic properties.

24. The method according to claim 1, wherein the determination of the change of the mechanical and/or viscoelastic properties of the inks and/or coating films on the substrate is performed for radiation-hardening ink and/or coating films that were hardened by UV radiation and/or electron beam drying.

25. The method according to claim 1, wherein the determination of the change of the mechanical and/or viscoelastic properties of the ink and/or coating films on the substrate is performed for solvent-containing or aqueous inks and/or coatings.

* * * * *